United States Patent
Ouchi et al.

(10) Patent No.: US 6,378,351 B1
(45) Date of Patent: Apr. 30, 2002

(54) METHOD FOR MANUFACTURING ENDOSCOPIC BIOPSY FORCEPS CUP

(75) Inventors: Teruo Ouchi, Saitama; Masaru Nagamine, Kagawa, both of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/665,059

(22) Filed: Sep. 19, 2000

(30) Foreign Application Priority Data

Sep. 30, 1999 (JP) .......................................... 11-278079

(51) Int. Cl.⁷ .............................................. B21D 28/10
(52) U.S. Cl. ............................ 72/336; 72/339; 606/207
(58) Field of Search .......................... 72/335, 336, 334, 72/337, 339, 329, 330, 324; 606/207, 205, 170

(56) References Cited

U.S. PATENT DOCUMENTS

| | | | | |
|---|---|---|---|---|
| 604,376 A | * | 5/1898 | Egge | 72/329 |
| 3,289,523 A | * | 12/1966 | Kramer | 72/330 |
| 4,291,567 A | * | 9/1981 | Murayama | 72/335 |
| 5,647,115 A | * | 7/1997 | Slater | 72/324 |

FOREIGN PATENT DOCUMENTS

| | | |
|---|---|---|
| JP | 3-26608 | 4/1991 |
| JP | 4-46730 | 11/1992 |
| JP | 5-54345 | 8/1993 |
| JP | 5-39684 | 10/1993 |
| JP | 9-276285 | 10/1997 |
| JP | 10-24045 | 1/1998 |
| JP | 11178829 | 7/1999 |

* cited by examiner

*Primary Examiner*—Daniel C. Crane
(74) *Attorney, Agent, or Firm*—Greenblum & Bernstein P.L.C.

(57) ABSTRACT

A method for manufacturing a biopsy forceps cup for an endoscope in which a spoon-shaped forceps cup is formed by drawing a metal plate blank by a press, includes forming a first cut on the metal plate blank, wherein the first cut surrounds a contour of a portion of the metal plate blank defining a forceps cup blank corresponding to the forceps cup, the first cut being discontinued by a plurality of first connection portions; forming a second cut on the metal plate blank, wherein the second cut surrounds the first cut, the second cut being discontinued by a plurality of second connection portions; and carrying out a drawing operation on the metal plate blank while each of the first and second connection portions remain connected with respective neighboring portions defined by each respective the first and second cuts.

14 Claims, 11 Drawing Sheets

METHOD FOR MANUFACTURING ENDOSCOPIC BIOPSY FORCEPS CUP

BACKGROUND OF THE INVENTION

1. Field of the Invention

The present invention relates to a method for manufacturing a cup of a cup biopsy forceps for an endoscope, which is inserted in a forceps channel of an endoscope to remove a specimen of tissue from a living body cavity for the purpose of diagnosis.

2. Description of the Related Art

In general, a cup biopsy forceps for an endoscope is provided with a pair of forceps cups in the form of spoons at a front end of a sheath thereof which is inserted in and removed from a forceps channel of an endoscope. The forceps cups are opened and closed, by pulling or extending an operation wire which extends within the sheath in the axial direction thereof, so that mucous membrane tissue can be bitten off and removed by cutting edges formed at the edges of the forceps cups.

In the past, the forceps cup has been formed by cutting a metal rod. However, the manufacturing cost is remarkably high, and hence, recently, forceps cups have been formed by pressing a plate (e.g., Japanese Unexamined Patent Publication No. 9-276285 and No. 10-24045).

In a known manufacturing method of an endoscopic biopsy forceps cup, a metal plate is punched along a contour of a cup blank, and the cup blank thus obtained is subject to a drawing operation using a press to produce a predetermined forceps cup.

When the flat metal plate is subject to the drawing operation using a press to obtain a predetermined shape of a forceps cup (substantially in the form of a spoon), the metal plate is entirely drawn toward the drawing portion. However, if the drawing resistance is not identical in all the directions, the amount of drawing is irregular.

Consequently, if the forceps cup blank which has been obtained by punching the metal plate along the contour of the forceps cup is subject to the drawing operation, the amount of drawing is not uniform in all directions. Thus, precise forceps cup cannot be produced, leading to a reduced cutting efficiency of the forceps cups.

SUMMARY OF THE INVENTION

It is an object of the present invention to provide a method for manufacturing a biopsy forceps cup for an endoscope which can be precisely formed by pressing a metal plate.

To achieve the object mentioned above, according to the present invention, a method is provided for manufacturing a biopsy forceps cup for an endoscope in which a spoon-shaped forceps cup is formed by drawing a metal plate blank by a press, the method including forming a first cut on the metal plate blank, wherein the first cut surrounds a contour of a portion of the metal plate blank defining a forceps cup blank corresponding to the forceps cup, the first cut being discontinued by a plurality of first connection portions; forming a second cut on the metal plate blank, wherein the second cut surrounds the first cut, the second cut being discontinued by a plurality of second connection portions; and carrying out a drawing operation on the metal plate blank while each of the first and second connection portions remain connected with respective neighboring portions defined by each respective the first and second cuts.

In an embodiment, the first connection portions are spaced from one another at a substantially equal distance, and the second connection portions are spaced from one another and are spaced from the first connection portions at a substantially equal distance.

In an embodiment, three connection portions constitute each of the first and second connection portions.

In an embodiment, one of the first connection portions is located at an end of the forceps cup blank in a longitudinal direction thereof, and wherein remaining two connection portions of the first connection portions are located at both ends of the forceps cup blank in a lateral direction thereof, perpendicular to the longitudinal direction.

In an embodiment, the first cut is provided with two first connection portions at both ends of the forceps cup blank in a longitudinal direction thereof, and the second cut is provided with two second connection portions at both ends of the forceps cup blank in a lateral direction thereof, perpendicular to the longitudinal direction.

In an embodiment, the first cut is provided with two first connection portions at both ends of the forceps cup blank in the lateral direction thereof, and the second cut is provided with two second connection portions at both ends of the forceps cup blank in a longitudinal direction thereof, perpendicular to the lateral direction.

Preferably, the second cut is provided spaced from the first cut at a constant distance around the first cut.

The first and second cuts can be formed by a press, or by laser cutting.

In an embodiment, after the drawing operation is completed, a piercing operation is carried out.

In an embodiment, after the piercing operation is completed, the first and second connection portions are cut, so that the forceps cup can be removed from the blank plate.

In an embodiment, the blank plate is placed on a female die whose contour corresponds to a cutting line of the forceps cup. A male die, whose contour corresponds to the female die, is pressed into the female die by a press to cut the forceps cup from the blank plate.

The present disclosure relates to subject matter contained in Japanese Patent Application No. 11-278079 (filed on Sept. 30, 1999) which is expressly incorporated herein by reference in its entirety.

BRIEF DESCRIPTION OF THE DRAWINGS

The present invention will be discussed below in detail, with reference to the accompanying drawings, in which.

DESCRIPTION OF THE PREFERRED EMBODIMENT

Figure 2:
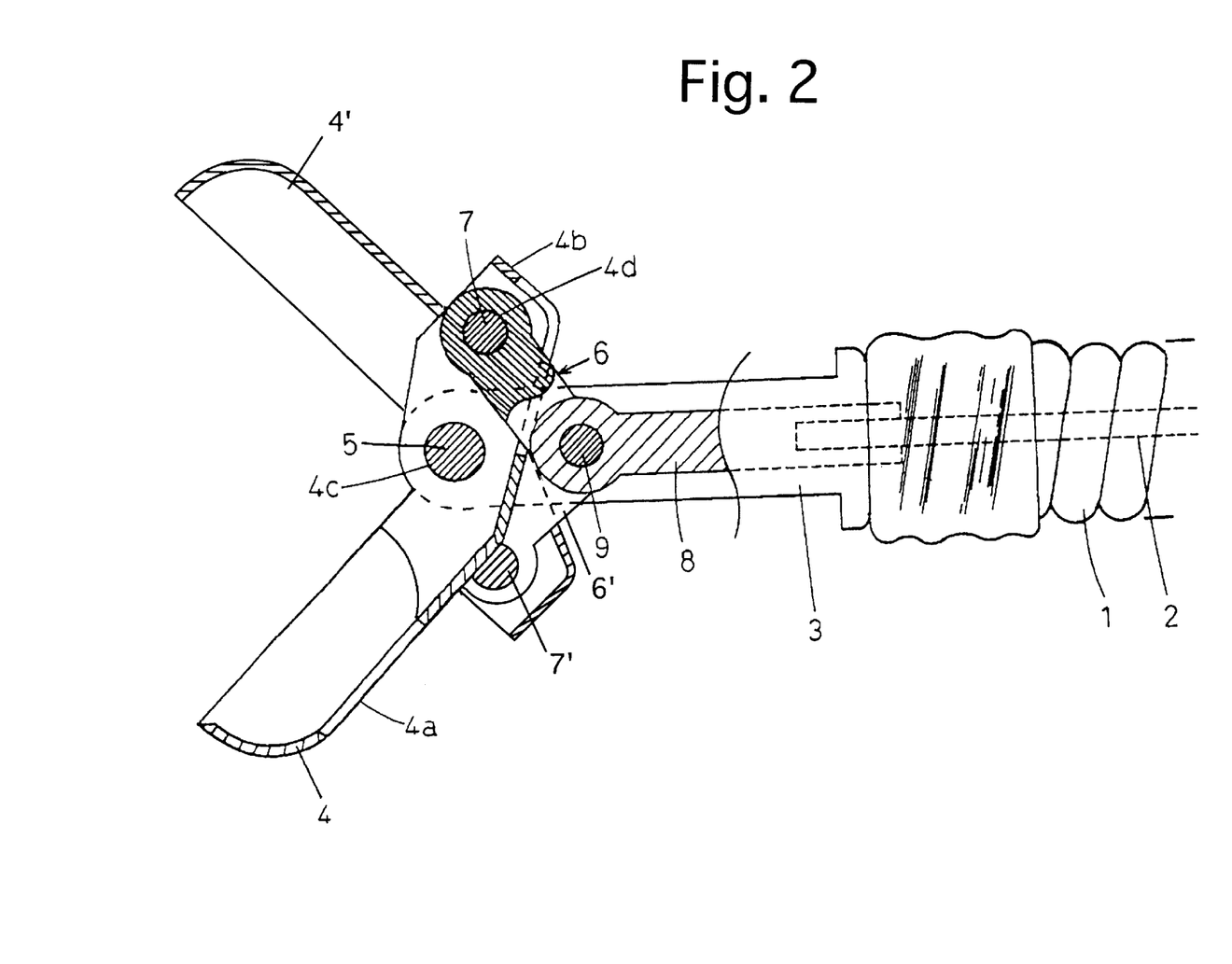
FIG. 2 is a side sectional view of a front end portion of an endoscopic biopsy forceps produced by a method according to the present invention.

In FIG. 2, which shows a front end portion of an endoscopic biopsy forceps, an operation wire 2 extends within a flexible sheath 1 which is formed by a closely wound coil of stainless wire, so as to move in the axial direction.

The sheath 1 is provided with a distal end body 3. A pair of forceps cups 4 and 4', which are rotatable about a pivot shaft 5, are provided on the front end of the distal end body 3. When the operation wire 2 is remotely pulled or extended at the proximal end thereof, the forceps cups 4 and 4' are opened and closed via link plates 6 and 6', respectively. A connection rod 8 is connected to a rear end of the link plates 6 and 6' by a rivet 9, connecting the operation wire 2 with the link plates 6 and 6'.

Figure 3:
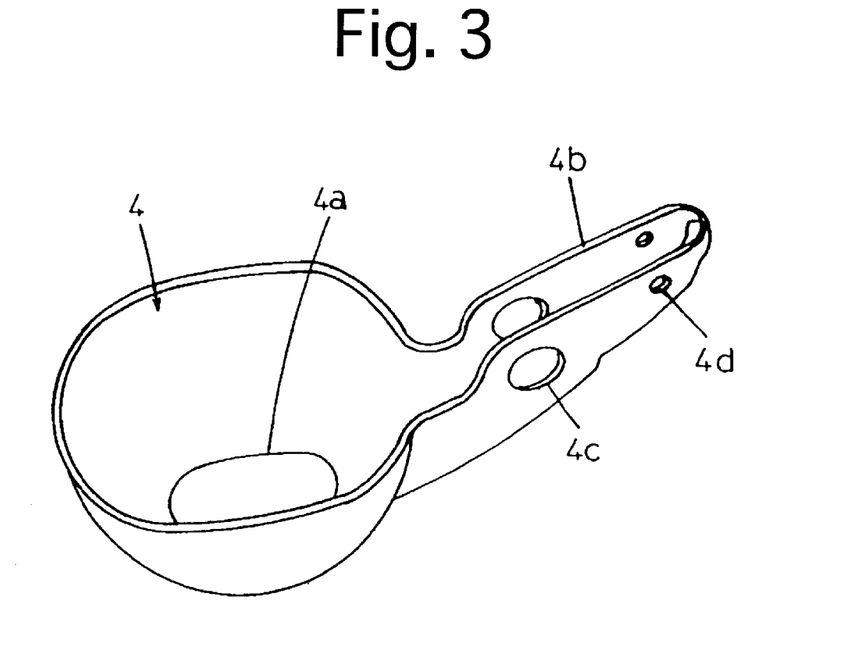
FIG. 3 is a perspective view of a forceps cup of a cup biopsy forceps for an endoscope produced by a method according to the present invention.

A forceps cup 4 shown in FIG. 3 is formed by drawing a stainless steel plate by a press and is provided with a front half, in the form of a cup. The forceps cup 4 is provided on its rear surface of the front half with a hole 4a.

The forceps cup is provided on its rear half with a link portion 4b which is in turn provided with fitting holes 4c, in which the pivot shaft 5 is fitted, and fitting holes 4d, in which the rivet 7 is fitted, to connect the link portion 4b to the link plate 6.

Figure 4:
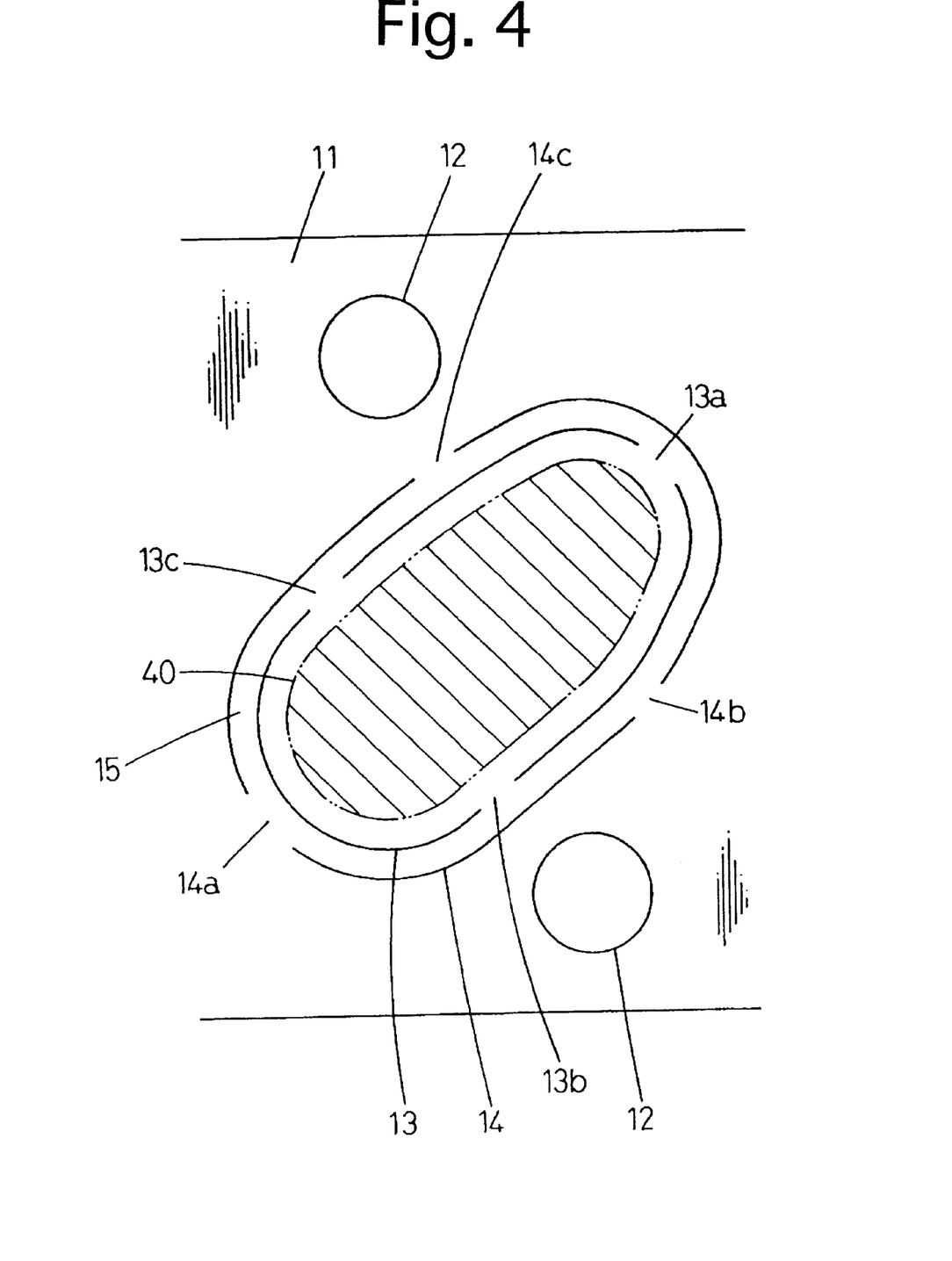
FIG. 4 is a plan view of an endoscopic biopsy forceps cup according to a first embodiment of the present invention before it has been drawn by a press.

FIG. 4 shows the first step of the manufacturing process to manufacture the forceps cup 4 from a single stainless steel plate. The blank plate 11 is a flat stainless steel plate. Positioning pins (not shown) are fitted through positioning holes 12 of the blank plate 11.

In FIG. 4, the portion of the blank plate 11 (forceps cup blank 40) corresponding to the forceps cup 4 is shown as a hatched area. A first cut 13 which is spaced from the contour of the forceps cup blank 40 at a predetermined distance is formed so as to surround the forceps cup blank 40. The first cut 13 is cut, for example, by a shearing operation by a press, or by laser cutting.

The first cut 13 is formed in a discontinuous cut line and is provided with non-cut portions 13a, 13b, and 13c (first connection portions) which connect the blank plate portion 11 located outside the first cut 13 and the forceps cup blank 40.

One of the first connection portions 13a, 13b and 13c (connection portion 13a in this embodiment) is located in the end of the longitudinal direction of the forceps cup blank 40, and the remaining two connection portions 13b and 13c are located in the lateral direction of the forceps cup blank 40 perpendicular to the longitudinal direction. The three first connection portions 13a, 13b and 13c are spaced from one another in the circumferential direction at a substantially equal distance.

A second cut 14 is provided spaced from the first cut 13 at a constant distance around the first cut. The second cut 14 is also formed in a discontinuous cut line and is provided with non-cut portions 14a, 14b, and 14c (second connection portions).

The three second connection portions 14a, 14b and 14c are spaced from one another and from the first connection portions 13a, 13b and 13c, in the circumferential direction at a substantially equal distance. Furthermore, the second connection portion 14a located in the longitudinal direction of the forceps cup blank 40 is located on the side opposite to the first connection porti on 13a located in the longitudinal direction. It should be noted that the first and second cuts can be carried out in one single process.

After the first and second cuts 13 and 14 are formed (cut) in the flat blank plate 11, the forceps cup blank portion 40 is subject to a drawing operation by a press to form a forceps cup 4.

Figure 1:
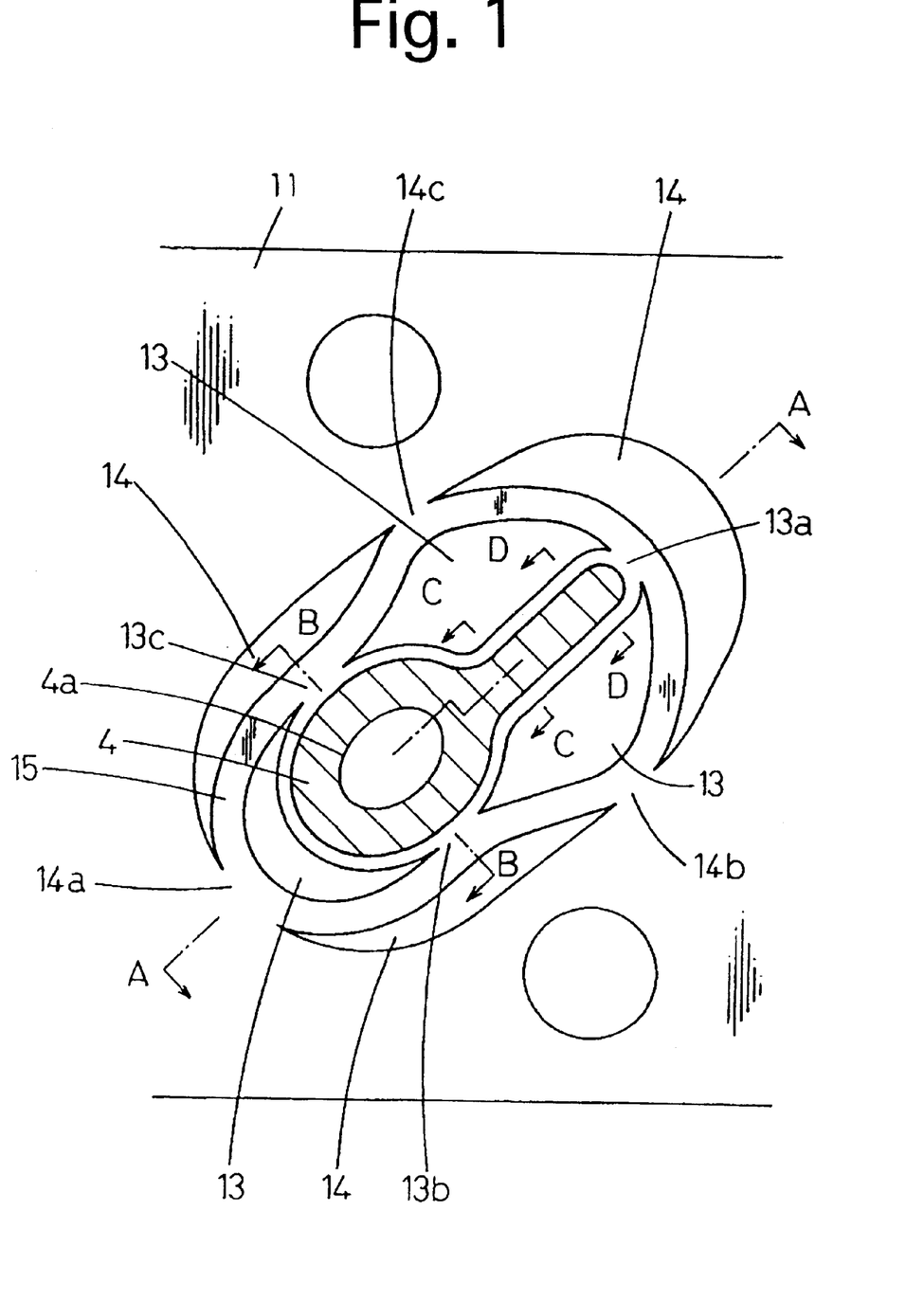
FIG. 1 is a plan view of an endoscopic biopsy forceps cup which has been drawn by a press, according to a first embodiment of the present invention.
Figure 5:
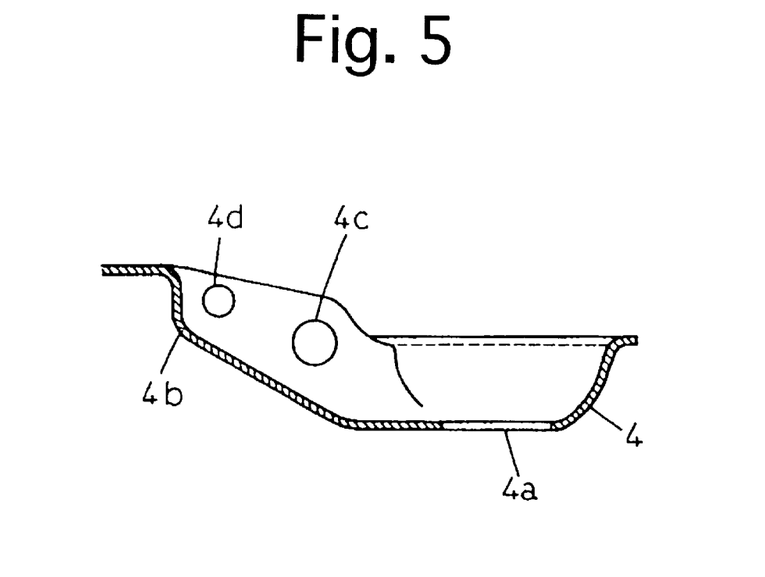
FIG. 5 is a sectional view taken along the line A—A in FIG. 1, showing an endoscopic biopsy forceps cup according to a first embodiment of the present invention after it has been drawn by a press.
Figure 6:
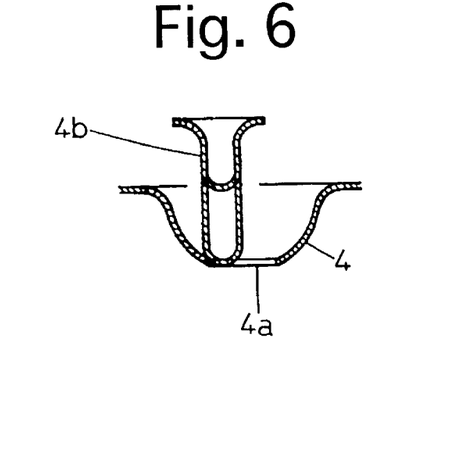
FIG. 6 is a composite sectional view taken along the lines B—B, C—C and D—D in FIG. 1, showing an endoscopic biopsy forceps cup according to a first embodiment of the present invention after it has been drawn by a press.

FIG. 1, the blank has been drawn by a press to form the forceps cup 4. FIG. 5 shows a sectional view taken along the line A—A in FIG. 1, and FIG. 6 shows a composite sectional view taken along the lines B—B, C—C and D—D in FIG. 1.

As shown in FIG. 1, since the blank portion 11 is drawn toward the drawing portion, the first and second cut portions 13 and 14 are deformed and opened, so that a band portion 15 defined between the first and second cut portions 13 and 14 is deformed and extended inward at the portions other than those corresponding to the second connection portions 14a, 14b and 14c.

Thus, upon drawing, the forceps cup blank 40 is connected to the blank plate 11 by the six connection portions, i.e., the first connection portions 13a, 13b and 13c which are spaced from one another at a substantially equal distance and the second connection portions 14a, 14b and 14c which are spaced from one another at a substantially equal distance, and hence, it is possible not only to precisely draw the forceps cup blank 40 which is positioned in place, but also to precisely form the forceps cup 4 due to a uniform drawing force applied to the blank during the drawing operation.

Figure 7:
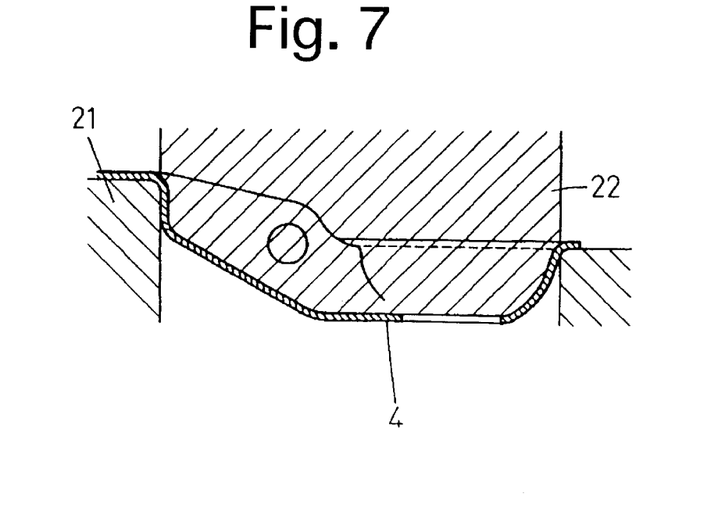
FIG. 7 is a composite sectional view taken along the line A—A, showing a cutting operation of an endoscopic biopsy forceps cup according to a first embodiment of the present invention after it has been drawn by a press.

After the drawing operation is completed, a piercing operation, etc., is carried out if necessary, and thereafter, the forceps cup 4 is cut from the blank plate 11. FIG. 7 shows a sectional view taken along the line A—A, and FIG. 8 shows a composite sectional view taken along the lines B—B, C—C and D—D.

Figure 8:
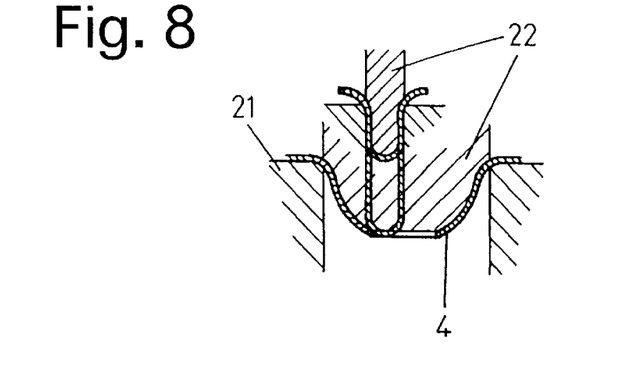
FIG. 8 is a composite sectional view taken along the lines B—B, C—C and D—D in FIG. 1, showing a cutting operation of an endoscopic biopsy forceps cup according to a first embodiment of the present invention after it has been drawn by a press.

As can be seen in FIGS. 7 and 8, the blank plate 11 is placed on a female die 21 whose contour corresponds to a cutting line of the forceps cup 4 along which the forceps cup is to be cut. A male die 22, whose contour corresponds to the female die 21, is pressed into the female die 21 by a press to cut the forceps cup 4 from the blank plate 11.

Thus, the cutting edge is formed along the cutting line of the forceps cup 4. Namely, the separation and formation of the cutting edge of the forceps cup 4 can be carried out by one operation.

Figure 9:
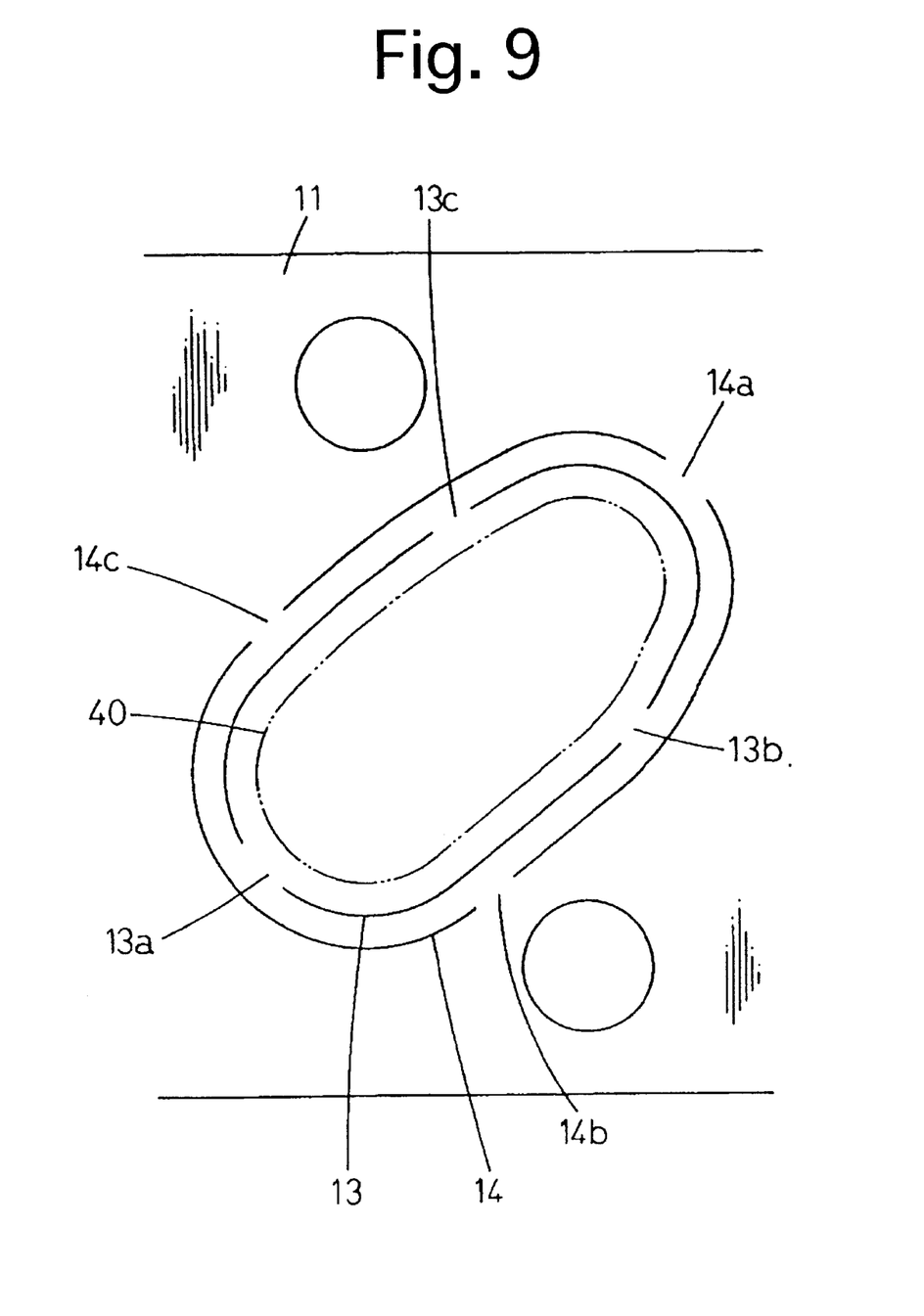
FIG. 9 is a plan view of an endoscopic biopsy forceps cup according to a second embodiment of the present invention before it has been drawn by a press.
Figure 10:
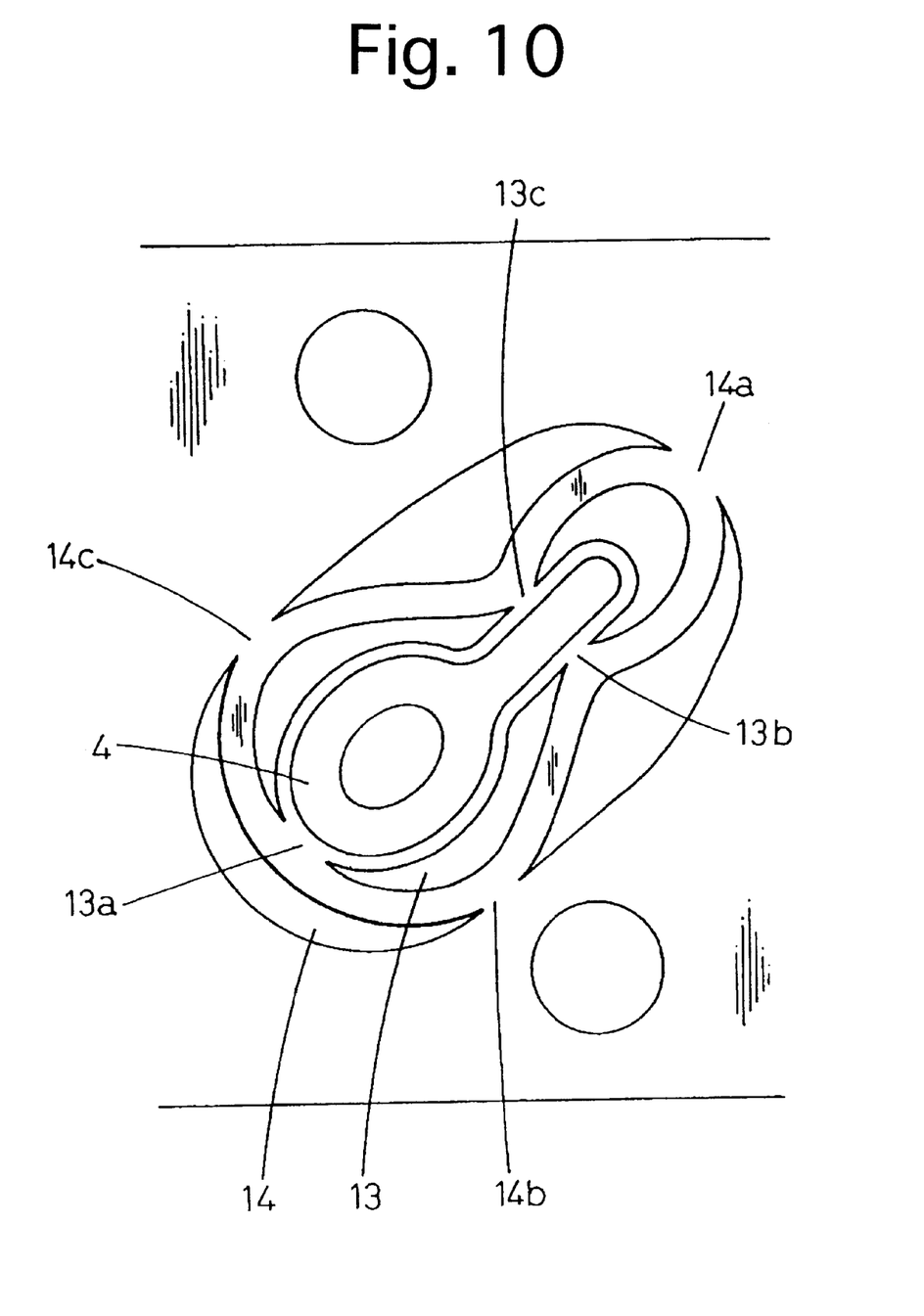
FIG. 10 is a plan view of an endoscopic biopsy forceps cup according to a second embodiment of the present invention after it has been drawn by a press.

FIGS. 9 and 10 show a blank plate 11 on which the first and second cuts 13 and 14 are formed according to a second embodiment of the present invention. In the second embodiment, as shown in FIG. 9, the phase of the three first connection portions 13a, 13b and 13c and the three second connection portions 14a, 14b and 14c is shifted in the longitudinal direction, by 180 degrees with respect to the first embodiment. FIG. 10 shows the blank plate which has been drawn by a press.

Figure 11:
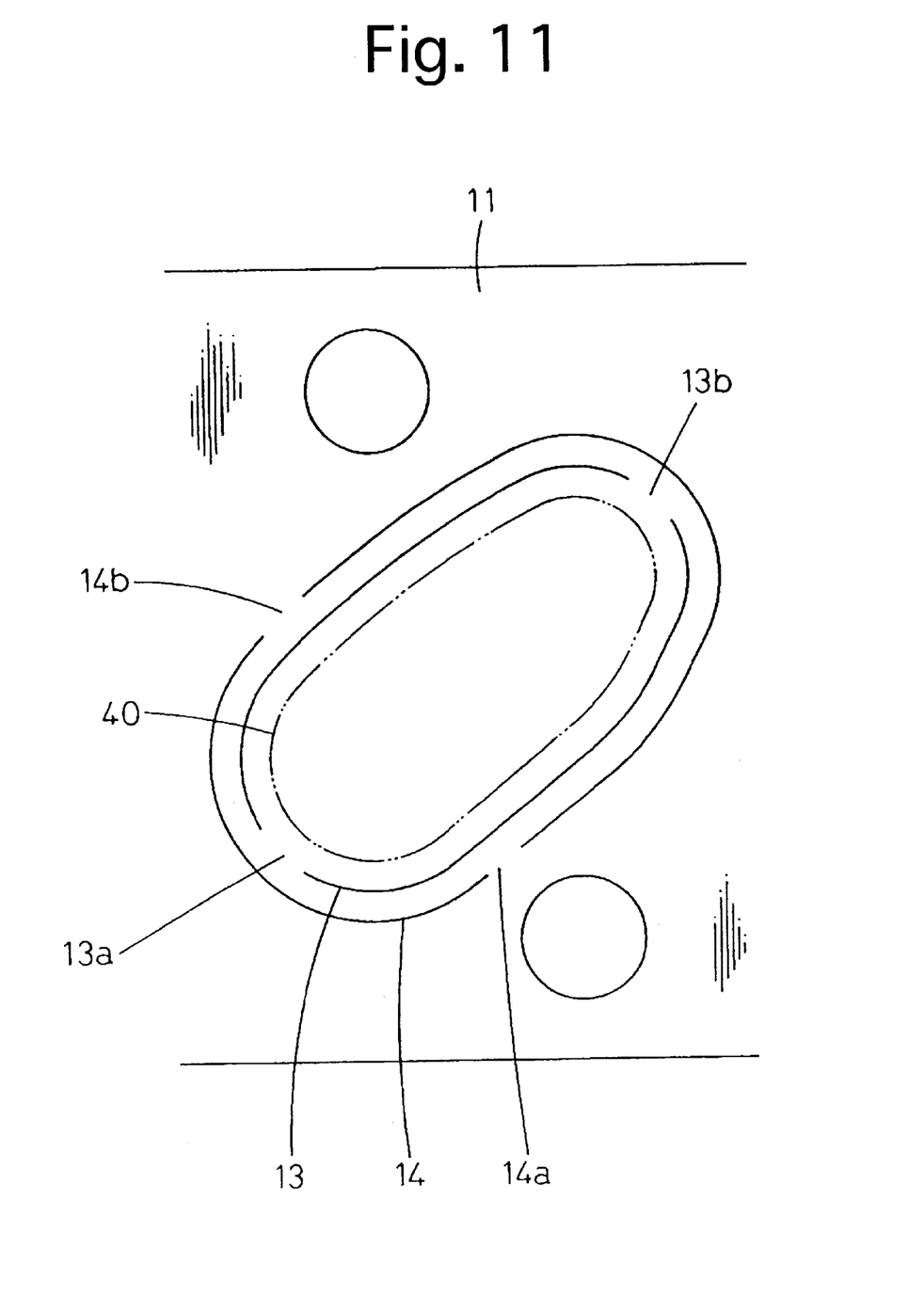
FIG. 11 is a plan view of an endoscopic biopsy forceps cup according to a third embodiment of the present invention before it has been drawn by a press.
Figure 12:
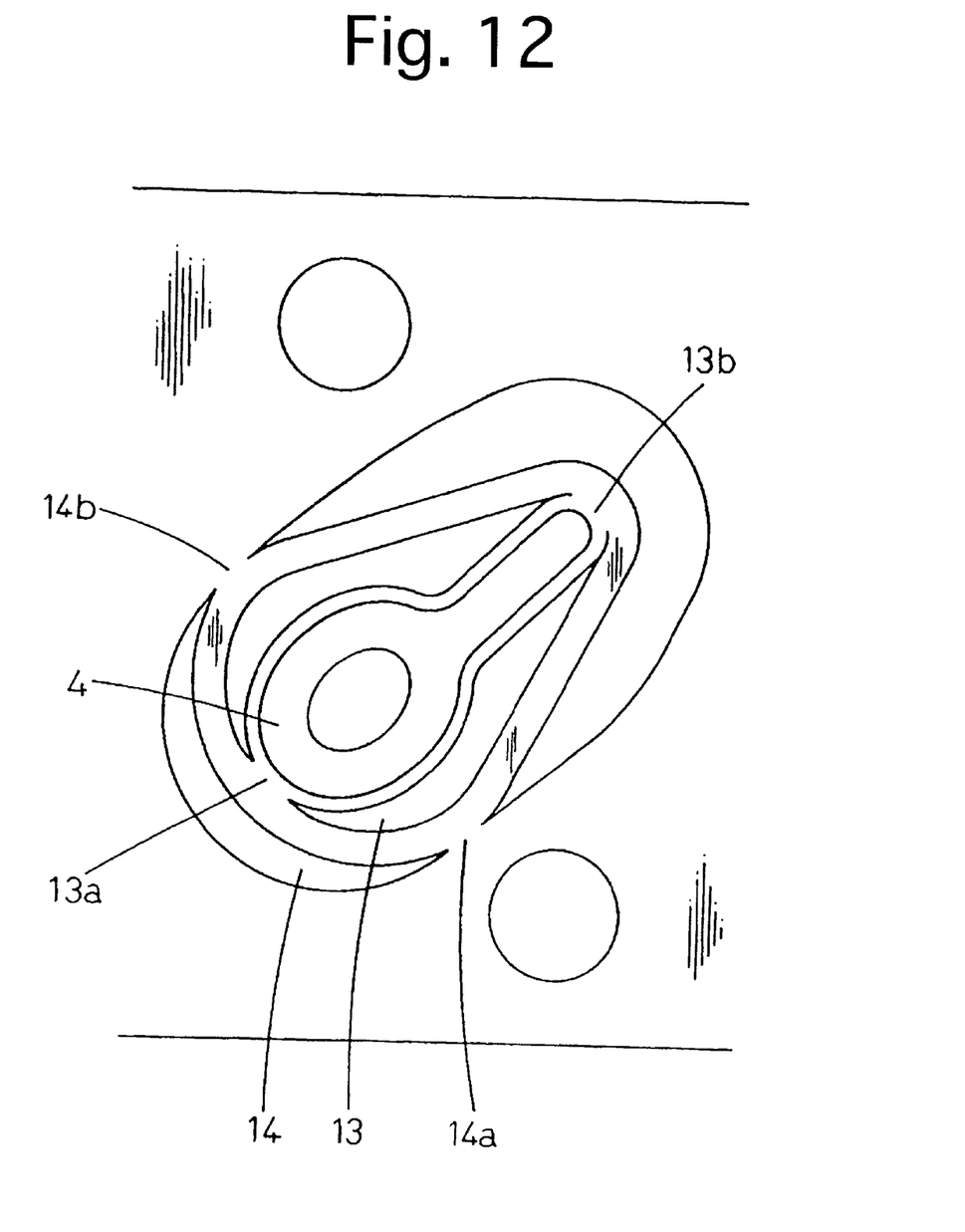
FIG. 12 is a plan view of an endoscopic biopsy forceps cup according to a third embodiment of the present invention after it has been drawn by a press.

FIGS. 11 and 12 show a blank plate 11 in which the first and second cuts 13 and 14 are formed according to a third embodiment of the present invention. In the third embodiment, as shown in FIG. 11, the first cut 13 is provided with two first connection portions 13a and 13b in the longitudinal direction, and the second cut 14 is provided with two second connection portions 14a and 14b in the direction perpendicular to the longitudinal direction. FIG. 12 shows the blank plate which has been drawn by a press.

Figure 13:
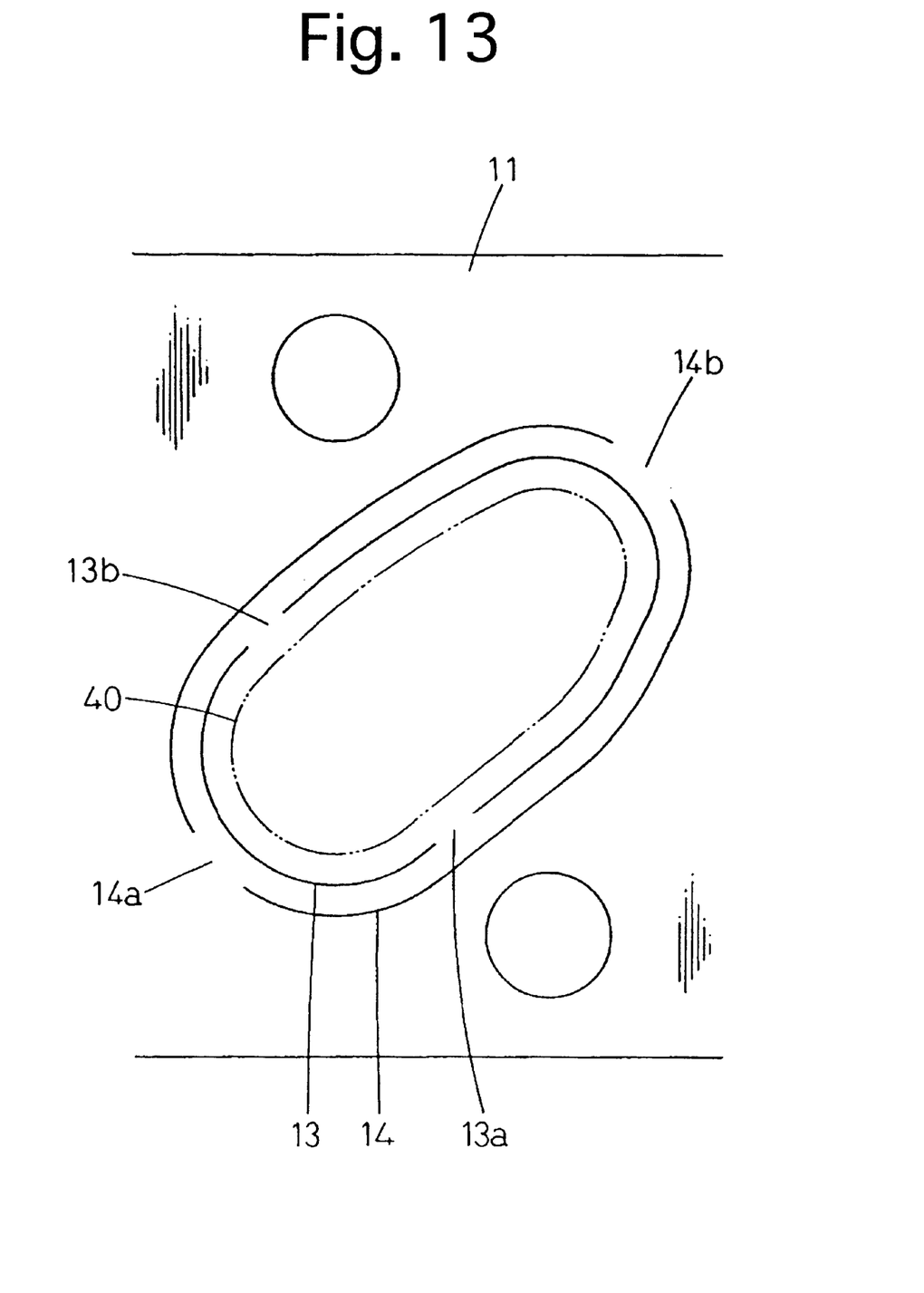
FIG. 13 is a plan view of an endoscopic biopsy forceps cup according to a fourth embodiment of the present invention before it has been drawn by a press.
Figure 14:
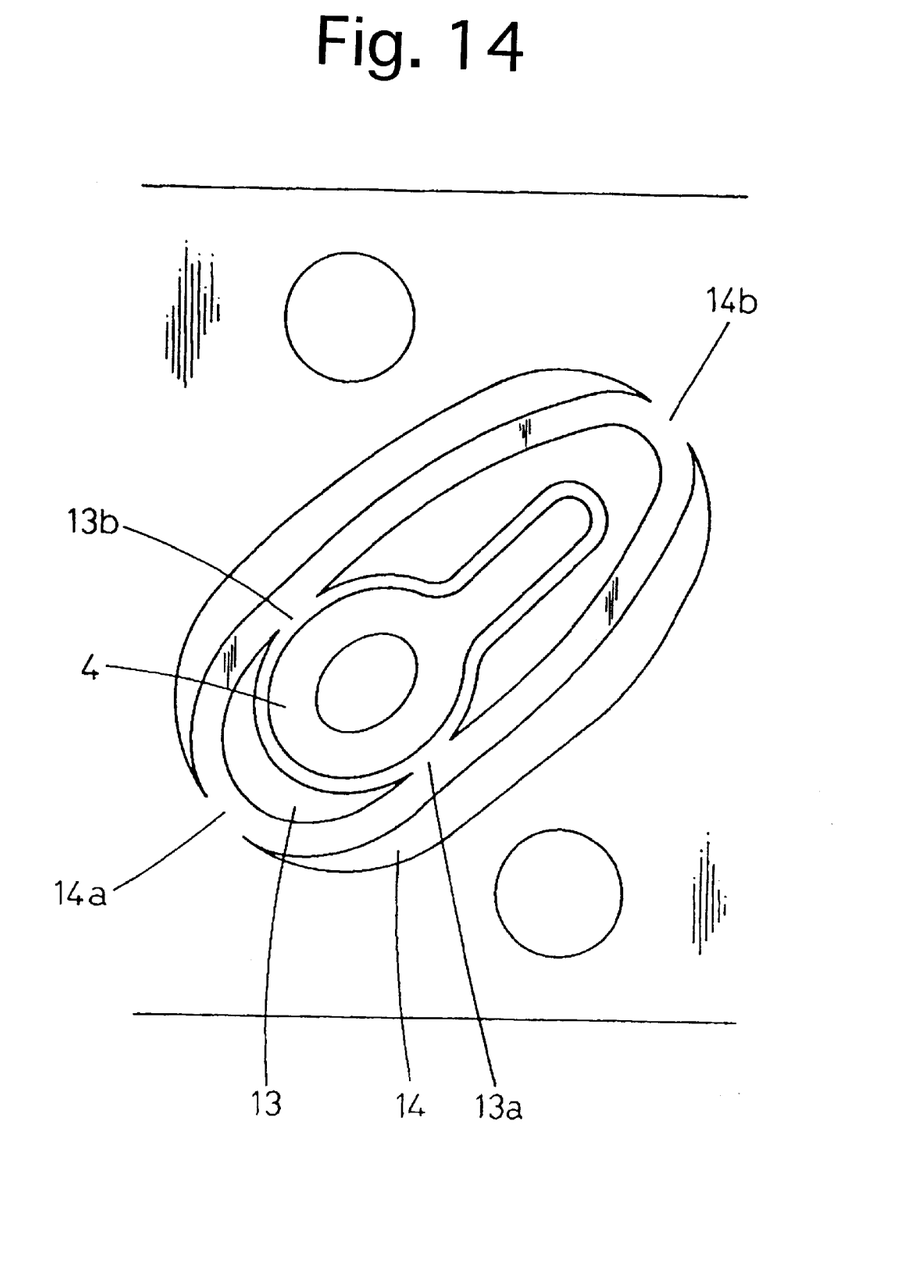
FIG. 14 is a plan view of an endoscopic biopsy forceps cup according to a fourth embodiment of the present invention after it has been drawn by a press.

FIGS. 13 and 14 show a blank plate 11 in which the first and second cuts 13 and 14 are formed according to a fourth embodiment of the present invention. In the fourth embodiment, as shown in FIG. 13, the second cut 14 is provided with two second connection portions 14a and 14b in the longitudinal direction, and the first cut 13 is provided with two first connection portions 13a and 13b in the direction perpendicular to the longitudinal direction. FIG. 14 shows the blank plate which has been drawn.

As can be understood from the above discussion, according to the present invention, since the first cut which surrounds the portion of the blank plate corresponding to the contour of the forceps cup and is discontinued by a plurality of first connection portions, and the second cut which surrounds the first cut and is discontinued by a plurality of second connection portions are formed in the blank plate before the drawing operation is carried out, the forceps cup blank is precisely held in a predetermined position during the drawing operation due to the connection portions. Consequently, the forceps cup can be precisely formed by a press operation.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A method for manufacturing a biopsy forceps cup for an endoscope in which a spoon-shaped forceps cup is formed by drawing a metal plate blank by a press, said method comprising:

forming a first cut on said metal plate blank, wherein said first cut surrounds a contour of a portion of said metal plate blank defining a forceps cup blank corresponding to said forceps cup, and said first cut is disconnected by a first connection portion that is formed close to an end of the arm portion of said forceps cup and by a second connection portion and a third connection portion that are formed close to a plurality of side portions of said forceps cup;

forming a second cut on said metal plate blank, wherein said second cut surrounds said first cut, said second cut being discontinued by a plurality of second connection portions; and carrying out a drawing operation on said metal plate blank to produce said forceps cup while each of said first and second connection portions remain connected with respective neighboring portions defined by each respective said first and second cuts.

2. A method for manufacturing a biopsy forceps cup for an endoscope according to claim 1, wherein said first connection portions are spaced from one another at a substantially equal distance, and said second connection portions are spaced from one another and are spaced from said first connection portions at a substantially equal distance.

3. A method for manufacturing a biopsy forceps cup for an endoscope according to claim 2, wherein three connection portions constitute each of said first and second connection portions.

4. A method for manufacturing a biopsy forceps cup for an endoscope according to claim 3, wherein one of said first connection portions is located at an end of said forceps cup blank in a longitudinal direction thereof, and wherein remaining two connection portions of said first connection portions are located at both ends of said forceps cup blank in a lateral direction thereof, perpendicular to said longitudinal direction.

5. A method for manufacturing a biopsy forceps cup for an endoscope according to claim 2, wherein said first cut is provided with two first connection portions at both ends of said forceps cup blank in a longitudinal direction thereof, and said second cut is provided with two second connection portions at both ends of said forceps cup blank in a lateral direction thereof, perpendicular to said longitudinal direction.

6. A method for manufacturing a biopsy forceps cup for an endoscope according to claim 2, wherein said first cut is provided with two first connection portions at both ends of said forceps cup blank in the lateral direction thereof, and said second cut is provided with two second connection portions at both ends of said forceps cup blank in a longitudinal direction thereof, perpendicular to said lateral direction.

7. A method for manufacturing a biopsy forceps cup for an endoscope according to claim 1, wherein said second cut is provided spaced from said first cut at a constant distance around said first cut.

8. A method for manufacturing a biopsy forceps cup for an endoscope according to claim 1, wherein said first and second cuts are formed by a press.

9. A method for manufacturing a biopsy forceps cup for an endoscope according to claim 1, wherein said first and second cuts are formed by laser cutting.

10. A method for manufacturing a biopsy forceps cup for an endoscope according to claim 1, wherein after said drawing operation is completed, a piercing operation is carried out.

11. A method for manufacturing a biopsy forceps cup for an endoscope according to claim 10, wherein after said piercing operation is completed, said first and second connection portions are cut, so that said forceps cup can be removed from said blank plate.

12. A method for manufacturing a biopsy forceps cup for an endoscope according to claim 10, wherein said blank plate is placed on a female die whose contour corresponds to a cutting line of said forceps cup; and wherein a male die, whose contour corresponds to said female die, is pressed into said female die by a press to cut said forceps cup from said blank plate.

13. A method for manufacturing a biopsy forceps cup for an endoscope in which a spoon-shaped forceps cup is formed by drawing a metal plate blank by a press, said method comprising:

forming a first cut on said metal plate blank, wherein said first cut surrounds a contour of a portion of said metal plate blank defining a forceps cup blank corresponding to said forceps cup, and said first cut is disconnected by a first connection portion that is formed close to an end opposite to the arm portion of said forceps cup and by a second connection portion and a third connection portion that are formed close to a plurality of side portions of the arm portion of said forceps cup;

forming a second cut on said metal plate blank, wherein said second cut surrounds said first cut, said second cut being discontinued by a plurality of second connection portions; and carrying out a drawing operation on said metal plate blank to produce said forceps cup while each of said first and second connection portions remain connected with respective neighboring portions defined by each respective said first and second cuts.

14. A method for manufacturing a biopsy forceps cup for an endoscope in which a spoon-shaped forceps cup is formed by drawing a metal plate blank by a press, said method comprising:

forming a first cut on said metal plate blank, wherein said first cut surrounds a contour of a portion of said metal plate blank defining a forceps cup blank corresponding to said forceps cup, and said first cut is disconnected by a first connection portion that is formed close to an end of the arm portion of said forceps cup and by a second connection portion that is formed close to an end opposite to the arm portion of said forceps cup;

forming a second cut on said metal plate blank, wherein said second cut surrounds said first cut, said second cut being discontinued by a plurality of second connection portions; and carrying out a drawing operation on said metal plate blank to produce said forceps cup while each of said first and second connection portions remain connected with respective neighboring portions defined by each respective said first and second cuts.

* * * * *